United States Patent [19]

Hartman et al.

[11] Patent Number: 4,593,033

[45] Date of Patent: Jun. 3, 1986

[54] SUBSTITUTED INDENO[2,1-C] PYRIDINES USEFUL AS CALCIUM CHANNEL BLOCKERS

[75] Inventors: George D. Hartman, Lansdale; Wasyl Halczenko, Hatfield; Steven D. Young, Lansdale, all of Pa.

[73] Assignee: Merck & Co., Inc., Rayway, N.J.

[21] Appl. No.: 726,746

[22] Filed: Apr. 24, 1985

[51] Int. Cl.[4] .................. A61K 31/435; A61K 31/44; C07D 221/16

[52] U.S. Cl. ..................................... 514/290; 546/111

[58] Field of Search ....................... 514/290, 253, 222; 546/111, 77, 64; 544/60, 126, 361

[56] References Cited

U.S. PATENT DOCUMENTS

| | | | |
|---|---|---|---|
| 3,574,686 | 4/1971 | Jucker et al. | 546/111 |
| 3,905,970 | 9/1975 | Bossert et al. | 260/247.2 |
| 3,923,818 | 12/1975 | Bossert et al. | 260/294.8 |
| 4,044,141 | 8/1977 | Bossert et al. | 424/266 |
| 4,237,137 | 12/1980 | Tacke et al. | 424/251 |
| 4,285,955 | 8/1981 | Wehinger et al. | 424/266 |

OTHER PUBLICATIONS

Angew. Chem. Int. Ed. Engl., 20 (1981) No. 9, Goldmann, S., pp. 779-780.
Weller et al., J. Org. Chem., 1983, 48, 3061-3067.
Schramm et al., Nature, vol. 303, Jun. 9th, 1983, pp. 535-537.
Bossert et al., Angew. Chem. Int. Ed. Eng., 762-769 (1981).
Goodman et al., Pharm. Basis of Therapeutics, 6 Ed., p. 28.

*Primary Examiner*—Henry R. Jiles
*Assistant Examiner*—J. Richter
*Attorney, Agent, or Firm*—Alice O. Robertson; R. Brent Olson; Joseph F. DiPrima

[57] ABSTRACT

Novel substituted indeno[2,1-c] pyridine compounds useful as calcium channel blockers, pharmaceutical compositions thereof, and methods of treatment are disclosed.

10 Claims, No Drawings

SUBSTITUTED INDENO[2,1-C] PYRIDINES USEFUL AS CALCIUM CHANNEL BLOCKERS

BACKGROUND OF THE INVENTION

Substituted dihydropyridines are known to be useful for reducing blood pressure, effecting dilation of the coronary vessels, and preventing urospasms. Typical of such substituted dihydropyridines are those disclosed in U.S. Pat. Nos. 3,923,818; 3,905,970; 4,044,141; 4,237,137; and 4,285,955. The substituted dihydropyridines disclosed in these patents do not include bridged ring structures.

Weller et al., [J. Org. Chem., 48, pp 3061-7 (1983)] disclose 1′-methylspiro[benzofuran-3-(2H)-4′-piperdine] as a substructure of morphine which is an early intermediate in a general synthesis of morphine but not possessing exceptional analgesic activity. Weller et al. also teach the preparation of spiro [benzofuran-3-(2H)-4′-(1′H)-pyridines] as potential intermediates in a synthesis of morphine but no biological activity of these compounds is reported.

Goldmann [Angew. Chem. Int. Ed. Engl., 20, pp. 779-780 (1981)] teaches the preparation of spiro[benzothiophene-1-oxide-4′-pyridines] as an intermediate in the preparation of 4,4-disubstituted 1,4-dihydropyridines.

SUMMARY OF THE INVENTION

This invention is directed to novel substituted indeno[2,1-c] pyridines and derivatives thereof and to methods for preparing such compounds. This invention is also directed to pharmaceutical compositions and methods of treatment for cardiovascular disorders in which high cellular concentration of $Ca^{++}$ is a factor.

DETAILED DESCRIPTION OF THE INVENTION

The specific substituted indeno[2,1-c] pyridine compounds of this invention are represented by the following general structural formula (I):

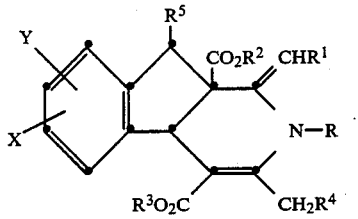

wherein:
R is hydrogen, $C_1$-$C_8$ alkyl or benzyl;
$R^1$ and $R^4$ independently are hydrogen, $C_1$-$C_8$ alkyl, $C_2$-$C_8$ alkenyl, $C_3$-$C_8$ cycloalkyl, $C_1$-$C_8$ hydroxyalkyl;
$R^2$ and $R^3$ independently are $C_1$-$C_8$ alkyl, $C_2$-$C_8$ alkenyl, $C_3$-$C_8$ cycloalkyl, $C_1$-$C_8$ hydroxyalkyl, $C_1$-$C_8$ dihydroxyalkyl, $C_2$-$C_8$ alkoxyalkyl, $C_3$-$C_8$ alkoxy(alkoxyalkyl), $C_1$-$C_8$ aminoalkyl wherein the amino group is $NR^6R^7$ in which $R^6$ and $R^7$ independently are hydrogen, $C_1$-$C_8$ alkyl, $C_7$-$C_{14}$ phenylalkyl or $R^6$ and $R^7$ together with the N atom form a 5 or 6 membered heterocycle selected from the group consisting of piperidinyl, morpholinyl, thiomorpholinyl, pyrrolidinyl, piperazinyl;
$R^5$ is hydrogen or $C_1$-$C_8$ alkyl; and
X and Y independently are hydrogen, $C_1$-$C_8$ alkyl, $C_1$-$C_8$ alkoxy, $CF_3$, cyano, nitro or halo, (i.e. fluoro, chloro or bromo) or X and Y together with the phenyl group to which they are attached form a naphthyl or benzoxadiazole group, and pharmaceutically acceptable salts thereof.

The preferred compounds of this invention are those represented by the general structural formula (I) wherein:
R is hydrogen or $C_1$-$C_8$alkyl;
$R^1$ and $R^4$ independently are hydrogen or $C_1$-$C_8$ alkyl;
$R^2$ and $R^3$ independently are $C_1$-$C_8$ alkyl or $C_1$-$C_8$ aminoalkyl wherein the amino group is $NR^6R^7$ in which $R^6$ and $R^7$ independently are hydrogen, $C_1$-$C_8$ alkyl or $C_7$-$C_{14}$ phenylalkyl;
$R^5$ is hydrogen or $C_1$-$C_8$ alkyl; and
X and Y independently are hydrogen, $C_1$-$C_8$ alkoxy, $CF_3$, cyano, nitro or halo.

The most preferred compounds of this invention are those preferred compounds wherein: $R^1$, $R^2$, $R^3$ and $R^4$ independently are hydrogen or $C_1$-$C_8$ alkyl and X and Y independently are hydrogen or $C_1$-$C_8$ alkoxy, halogen (preferably chloro, bromo, fluoro) or nitro and $R^5$ is hydrogen or methyl.

The compounds of this invention possess asymmetric centers and thus can exist in different isomeric forms. All such forms are included within the scope of this invention. Specifically, the compounds have an asymmetric center at the carbon atom to which the ester moiety, $-CO_2R^2$, is attached.

The compounds of the formula (I) wherein R is hydrogen exist as an equilibrium mixture of the tautomers of the formulae (I) and (Ia) as shown below.

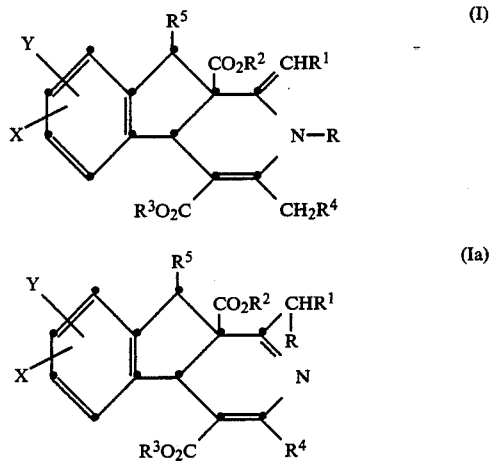

Illustrative of the compounds of this invention are the following compounds of the formula (I) and (Ia) which are the α-isomer, the β-isomer or mixtures thereof:

(1) Dimethyl 1-methylidene-3-methyl-2,4a-dihydro-9H-indeno[2,1-c]pyridine-4,9a-dicarboxylate [Formula (I) where R and $R^1$ and hydrogen, $R^2$, and $R^3$ and $R^4$ are methyl, $R^5$ is hydrogen, and X and Y are hydrogen] and Dimethyl 1,3-dimethyl-4a,9-dihydroindeno[2,1-c]pyridine-4,9a-dicarboxylate [Formula (Ia) where R and $R^1$ are hydrogen, $R^2$, $R^3$ and $R^4$ are methyl, $R^5$ is hydrogen and X and Y are hydrogen];

(2) Dimethyl 1-methylidene-3-methyl-6-chloro-2,4a-dihydro-9H-indeno[2,1-c]pyridine-4,9a-dicarboxylate[-Formula (I) where R and $R^1$ are hydrogen, $R^2$, $R^3$ and $R^4$ are methyl, $R^5$ is hydrogen, X is 6-chloro and Y is hydrogen] and Dimethyl 1,3-dimethyl-6-chloro-4a,9-dihydroindeno[2,1-c]pyridine-4,9a-dicarboxylate [Formula (Ia) where R and $R^1$ are hydrogen, $R^2$, $R^3$ and $R^4$ are methyl, $R^5$ is hydrogen, X is 6-chloro and Y is hydrogen]; and (3) Dimethyl 1-methylidene-3,9-dimethyl-6-methoxy-2,4a-dihydro-9H-indeno[2,1-c]pyridine-4,9a-dicarboxylate [Formula (I) where R and $R^1$ are hydrogen, $R^2$, $R^3$, $R^4$ and $R^5$ are methyl, X is 6-methoxy and Y is hydrogen] and Dimethyl 1,3,9-trimethyl-6-methoxy-4a,9-dihydroindeno[2,1-c]pyridine-4,9a-dicarboxylate [Formula (Ia) where R and $R^1$ are hydrogen, $R^2$, $R^3$, $R^4$ and $R^5$ are methyl, X is 6-methoxy and Y is hydrogen].

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic and trichloroacetic and the like and include acids related to the pharmaceutically acceptable salts listed in Journal of Pharmaceutical Science, 66, 2 (1977) and incorporated herein by reference.

The compounds of this invention are conveniently prepared from known or readily obtainable starting materials utilizing the general synthetic Pathways A and B described below:

Pathway A

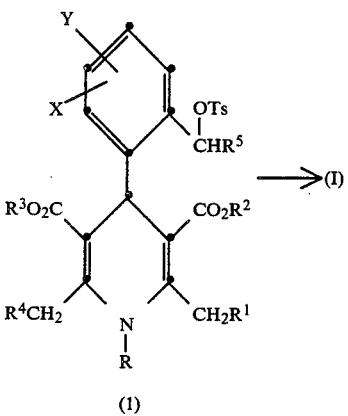

(1)

The dihydropyridine (1), wherein R, $R^1$, $R^2$, $R^3$, $R^4$, $R^5$, X and Y are described above and Ts is a tosyl radical, is treated between 0° and 150° C., preferrably 90° C. to 110° C. with between 1 and 100 equivalents, preferrably 10 to 20 equivalents, of base in an inert solvent under anhydrous conditions. Example of such bases are alkali metal carbonates, such as potassium carbonate and sodium carbonate, and lithium carbonate. Exemplifying the inert solvents employed in this cyclization are ethers, chlorinated hydrocarbons, aromatic hydrocarbons and amides. The preferred base is potassium carbonate and the preferred solvent is dimethylformamide.

Pathway B

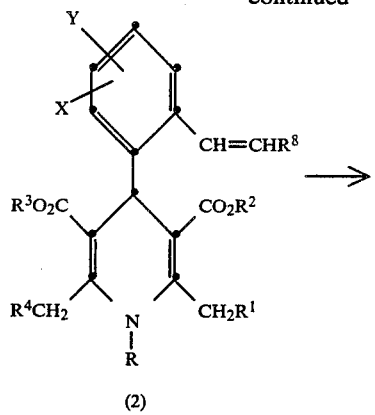

(2)

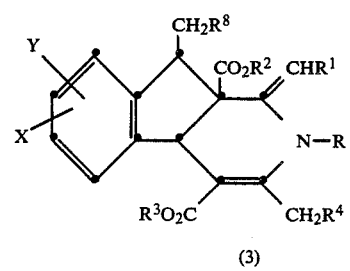

(3)

The dihydropyridine (2), wherein R, $R^1$, $R^2$, $R^3$, $R^4$, and X and Y are defined above, $R^8$ is hydrogen or $C_1$-$C_7$ alkyl, is treated under anhydrous conditions at between $-10°$ and 50° C., preferably at $-5°$ to 0° C., with between 1 and 10 equivalents, preferably a 2-fold excess, of a protic acid in an inert solvent to yield the cyclized compound (3). Examples of such anhydrous protic acids include gaseous hydrogen chloride and gaseous hydrogen bromide. Exemplifying the inert solvents employed in this cyclization reaction are ethers, chlorinated hydrocarbons, and aromatic hydrocarbons. Preferred solvents are methylene chloride, chloroform, benzene and toluene.

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) protection of the ischemic myocardium; and (vii) inhibition of irritable bowel syndrome and esophageal spasm. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace membrane bound tritiated nitrendepine.

The compounds of the present invention can be administered in any suitable form; e.g. orally, sublingually, transdermally, or parenterally; i.e. intravenously, interperitoneally, etc. Thus, the compounds can be offered in a form (a) for oral administration e.g. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified.

The pharmaceutical preparations thus described are made following the conventional techniques of the pharmaceutical chemist as appropriate to the desired end product.

The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or $\beta$-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for preparing the compounds and compositions of this invention, but are not to be construed as limiting this invention in any manner.

EXAMPLE 1

Preparation of [4a(R,S), 9a(S,R)]Dimethyl-1-methylidene-3-methyl-2,4a-dihydro-9H-indeno[2,1-c]pyridine-4,9a-dicarboxylate (a) o-bromomethylbenzyl alcohol (1a)

To a 3 neck 1-liter round bottomed flask equipped with a stirring bar, argon inlet, and pressure equalizing dropping funnel was added o-bromomethylbenzoic acid (35 g, 163 mmol) and 70 ml of dry tetrahydrofuran (THF). The slurry-solution was cooled in a 0° C. ice-salt bath and the dropping funnel was charged with a solution of borane in THF (212 ml of a 1.0 M solution, 212 mmol). This solution was added to the cold acid mixture, dropwise over 1 hour. When the addition was complete, the cooling bath was removed and the mixture was allowed to warm to room temperature and stir for 1 hour. The reaction was then quenched by careful addition of water (200 ml). The resulting solution was diluted with 600 ml of ether which resulted in a phase separation. The organic layer was separated and washed: $H_2O$ ($2 \times 500$ ml) and brine ($1 \times 500$ ml). Drying ($MgSO_4$), filtration, and removal of the solvent in vacuo left 25 g of a solid which was recrystallized from boiling ethyl acetate-hexane to give the compound (1a): mp 61°–63° C.; 'H NMR ($CDCl_3$) $\delta$2.05 (s, 1H), 4.60 (s, 2H), 4.80 (s, 2H), 7.20–7.55 (m, 4H).

(b) o-acetoxymethylbenzylalcohol (1b)

To a 100 ml round bottomed flask with magnetic stirring bar and argon inlet was added compound 1(a) (1.46 g, 7.26 mmol) and 20 ml of dry DMF. To this solution was added anhydrous sodium acetate (2.00 g, 23.51 mmol) and the mixture was stirred at room temperature for 8 hours. The reaction mixture was partitioned between ether (200 ml) and water (200 ml). The organic phase was separated and washed with water ($2 \times 100$ ml) and brine ($1 \times 100$ ml). Drying ($MgSO_4$, filtration, and removal of the solvent in vacuo gave 1.06 g of crude product. This material was chromatographed on 50 g of silica gel using 30% ethylacetate-70% hexane as the eluant to give the compound (1b) alcohol as a colorless oil: 'H-NMR ($CDCl_3\delta$) 2.00 (s, 3H), 2.75 (br s, 1H), 4.65 (s, 2H), 5.15 (s, 2H), 7.30 (m, 4H).

(c) o-acetoxymethylbenzaldehyde (1c)

To a 100 ml round bottom flask with a stirring bar, was added the compound 1(b) (500 mg, 2.77 mmol and 10 ml of methylene chloride. To this solution was added finely powdered, pyridinium chlorochromate (897 mg, 4.16 mmol). The mixture was stirred for 2.5 hour at room temperature, and was then filtered through a plug of silica gel. The tarry residue was triturated with ether, filtered, and the combined filtrates were concentrated in vacuo. This provided the compound (1c) as a colorless oil which was homogeneous by TLC analysis: 'H NMR ($CDCl_3$) $\delta$2.10 (s, 3H), 5.58 (s, 2H), 7.50 (m, 3H), 7.85 (m, 1H), 10.25 (s, 1H).

(d) Dimethyl 2,6-dimethyl-4-(2-acetoxymethylphenyl)-1,4-dihydropyridine-3,5-dicarboxylate (1d)

To a 100 ml round bottom flask containing the compound (1c) (473 mg, 2.65 mmol) was added a stirring bar, methyl acetoacetate (308 mg, 2.65 mmol), methyl 2-aminocrotonate (306 mg, 2.65 mmol) and 2-propanol (10 ml). This mixture was heated at reflux for 17 hours, cooled to room temperature and concentrated in vacuo. The crude product thus obtained was chromatographed on 50 g of silica gel using 30% ethyl acetate in 70% hexanes as the eluant, to give crystalline compound (1d). An analytical sample was prepared by recrystallization from boiling ethyl acetate: mp 149°–151° C. 'H NMR ($CDCl_3$) $\delta$2.21 (s, 3H), 2.35 (s, 6H), 3.55 (s, 6H), 4.90 (s, 1H), 5.45 (s, 2H), 5.90 (br s, 1H), 7.00–7.40 (m, 4H). Anal. Calcd. for $C_{20}H_{23}NO_6$: C, 64.33; H, 6.21; N, 3.75. Found: C, 64.51; H, 6.34; N, 3.93.

(e) Dimethyl 2,6-dimethyl-4-(2-hydroxymethylphenyl)-1,4-dihydropyridine-3,5-dicarboxylate (1e)

To a 100 ml round bottomed flask with a magnetic stirring bar was added the compound (1d) (1.27 g, 3.40 mmol) methanol (50 ml), and powdered anhydrous potassium carbonate (14 mg, 1 mmol). The mixture was stirred for 5 hours at room temperature. The reaction mixture was then diluted with ether (200 ml) and was washed with water (2×75 ml) and brine (1×100 ml). Drying (MgSO$_4$), filtration and removal of the solvent in vacuo. Recrystallization of the residue from boiling ethyl acetate-hexanes gave the compound (1e) as white crystals: mp 218°–220° C. 'H NMR (CDCl$_3$) δ2.25 (s, 6H), 3.55 (s, 6H), 4.35 (br d, 1H, J=6 Hz), 4.85 (d, 2H, J=6 Hz), 5.13 (s, 1H), 5.93 (br s, 1H), 7.00–7.40 (m, 4H). Anal. Calcd. for C$_{18}$H$_{21}$NO$_5$: C, 65.24; H, 6.39; N, 4.23. Found: C, 65.44; H, 6.41; N, 4.41.

(f) Dimethyl 2,6-dimethyl-4-(2-tosyloxymethylphenyl)-1,4-dihydropyridine-3,5-dicarboxylate (1f) and [4a(R,S), 9a(S,R)]Dimethyl 1-methylidene-3-methyl-2,4a-dihydro-9H-indeno[2,1c-]pyridine-4,9a-dicarboxylate To a 100 ml round bottomed flask with a stirring bar was added the compound (1e) (632 mg, 1.90 mmol), methylene chloride (30 ml) and P-toluenesulfonyl chloride (400 mg, 2.09 mmol). This solution was cooled to 0° C. and triethylamine (1g, 10.00 mmol) and 4-dimethylaminopyridine (5 mg, 0.04 mmol) were added. The cooling bath was allowed to expire and the mixture warmed to room temperature over 5 hours. The reaction mixture was diluted with chloroform and washed with 5% aqueous HCl, and brine. Drying (MgSO$_4$), filtration and removal of the solvent in vacuo gave a yellow oil. This material was chromatographed on 50 g of silica gel using 1:1 ethyl acetate-hexanes as the eluant, providing the compound (1f). 'H NMR (CDCl$_3$) δ2.23 (s, 6H), 2.40 (s, 3H), 3.47 (s, 6H), 4.90 (s, 1H), 5.56 (s, 2H), 6.25 (br s, 1H), 7.05–7.45 (m, 6H), 7.90 (d, 2H, J=9 Hz).

To a 100 ml round bottomed flask containing the compound (1f) (987 mg, 1.85 mmol) was added a stirring bar, dry DMF (20 ml), and finely powdered anhydrous potassium carbonate (2.56 g, 18.5 mmol), under argon. The flask was equipped with a reflux condenser and the mixture was heated in an oil bath at 110° C. for 2.75 hours with vigorous stirring. The cooled reaction mixture was diluted with ethyl acetate (300 ml) and washed with water (4×50 ml) and brine (100 ml). Drying (MgSO$_4$), filtration and removal of the solvent in vacuo left a brown oil which was crystallized from ethyl acetate. A more pure product was obtained by chromatography on 25 g of silica gel using 1:3 ethyl acetate-hexanes as the eluant followed by recrystallization from hot ethyl acetate-hexanes: mp 185°–188° C. IR (CHCL$_3$) 3440, 3000, 1735, 1690, 1610, 1250 cm$^{-1}$'H NMR (CDCl$_3$) δ2.35 (s, 3H), 3.29 (d, 1H, J=13.5 Hz), 3.60 (d, 1H, J=13.5 Hz), 3.65 (s, 3H), 3.75 (s, 3H), 4.32 (d, 1H, J=2 Hz), 4.48 (d, 1H, J=2 Hz), 4.65 (s, 1H), 6.09 (br s, 1H), 7.05 (m, 4H). Anal. Calcd. for C$_{18}$H$_{19}$NO$_4$: C, 69.00; H, 6.11; N, 4.47. Found: C, 69.20, 'H, 6.17; N, 4.80.

EXAMPLE 2

Preparation of [4a(R,S), 9a(S,R)]Dimethyl 1-methylidine-3-methyl-6-chloro-2,4a-dihydro-9H-indeno[2,1-c]pyridine-4,9a-dicarboxylate (a) 2-bromo-4-chlorobenzyl bromide (2a)

To a 500 ml 3-necked pyrex round bottomed flask equipped with a magnetic stirring bar, reflux condenser and argon inlet was added 2-bromo-4-chlorotoluene (10.00 g, 48.67 mmol), N-bromosuccinimide (18.66 g, 48.67 mmol) and dry, degassed carbon tetrachloride (200 ml). The stirred mixture was heated at reflux while being irradiated at a distance 10 cm by a 150 watt Hanovia low pressure mercury Lamp for 4 hours. The cooled reaction mixture was diluted with carbon tetrachloride and washed with water (2×200 ml) and brine (400 ml). Drying (MgSO$_4$), filtration, and removal of the solvent in vacuo left compound (2a) as a colorless oil. HPLC analysis indicates the material to be approximately 80% of the monobromo and 20% of the dibromo material. 'H NMR (CDCl$_3$) δ4.55 (s, 2H), 7.00–7.65 (m, 3H).

(b) 2-bromo-4-chlorodibenzyl ether (2b)

To a 300 ml 3-necked round bottomed flask equipped with a pressure equalizing dropping funnel, argon inlet, septum, and reflux condenser was added sodium hydride (3.67 g of a 50% oil dispersion, 76.5 mmol) and the oil was removed by two washings with 20 ml of hexanes. To the oil free sodium hydride was added dry DMF (80 ml), and a solution of benzyl alcohol (8.27 g, 76.5 mmol) in DMF (10 ml) was added dropwise over 30 minutes. The mixture was stirred and when H$_2$ had ceased a solution of the compound (2a) (14.5 g, 51.0 mmol) in DMF (10 ml) was added to the mixture, dropwise over 10 minutes. The resulting solution was warmed to 90° C. and stirred for 17 hours. The cooled reaction mixture was diluted with ether (600 ml), and washed with water (2×1000 ml) and brine (500 ml). Drying (MgSO$_4$), filtration, and removal of the solvent in vacuo left 16.5 g of a mixture of the compound (2b) and benzyl alcohol. This mixture was distilled through a 10 cm vigreux column to provide pure compound (2b): bp 150°–159° C. (0.20 torr). 'H NMR (CDCl$_3$) δ4.55 (s, 2H), 4.60 (s, 2H), 7.20–7.60 (m, 8H).

(c) 2-benzyloxymethyl-5-chlorobenzaldehyde (2c)

To a solution of the compound (2b) (6.62 g, 21.24 mmol) in dry THF (60 ml), cooled to −78° C. was added n-butyllithium (8.52 ml of a 2.7 m solution in hexanes, 23.0 mmol) with a syringe pump over 2 hours. To this solution was added N-formylpiperidine (2.40 g, 21.24 mol) neat dropwise with a syringe pump at such a rate that the temperature did not exceed −70° C. (ca. 2h). When the addition was complete, the cooling bath was removed and the mixture was warmed to room temperature over 0.5 hours. The mixture was then diluted with ether and washed with 2N HCl, saturated aqueous NaHCO$_3$, and brine. Drying (MgSO$_4$), filtration, and removal of the solvent in vacuo left 5.71 g (108%) of crude compound (2c) which was used without further purification. 'H NMR (CDCl$_3$) δ4.61 (s, 2H), 4.90 (s, 2H), 7.30 (br s, 5H), 7.55 (br s, 2H), 7.80 (s, 1H), 10.13 (s, 1H).

(d) Dimethyl 2,6-dimethyl-4-(2-benzyloxymethyl-5-chlorophenyl)-dihydropyridine-3,5-dicarboxylate (2d)

To a 250 ml round bottomed flask was added the compound (2c) (5.70 g, 22.90 mmol), methyl acetoacetate (2.66 g, 22.90 mmol), methyl 3-aminocrotonate (2.64 g, 22.90 mmol) and 2-propanol (30 ml). The flask was equipped with a stirring bar, reflux condenser and argon inlet and the mixture was heated at reflux for 20 hours with stirring. The reaction mixture was cooled to room temperature and the solvent was removed in vacuo. The crude product was chromatographed on 300 g of silica gel using 1:3 ethyl acetate-hexanes as eluant. The yellow oil obtained from the chromatography was triturated with ethyl ether and the resulting crystals of pure compound (2d) were collected on a first and dried. mp 156–158° C. $^1$H NMR (CDCl$_3$) δ2.26 (s, 6H), 3.50 (s, 6H), 4.69 (s, 2H), 4.95 (s 2H), 5.00 (s, 1H), 5.95 (br s, 1H), 7.00–7.60 (m, 8H).

Anal. Calcd. for C$_{25}$H$_{26}$ClNO$_5$: C., 65.86; H, 5.75; N, 3.07. Found: C, 66.08; H, 5.87; N, 3.29.

(e) Dimethyl 2,6-dimethyl-4-(2-hydroxymethyl-5-chlorophenyldihydropyridine-3,5-dicarboxylate (2e)

To a 250 ml round bottom flask with stirring bar was added the compound (2d) (2.00 g, 4.39 mmol), methanol (100 ml) and 10% palladium on carbon (200 mg). Hydrogen gas was bubbled through the vigorously stirred mixture until thin layer chromatographic analysis (3:7 ethyl acetate-hexane) indicated complete consumption of the starting material (ca. 2 h). The reaction mixture was filtered through a celite pad and the solvent was removed in vacuo. This procedure gave the off-white crystalline compound (2e). An analytical sample was obtained by recrystallization of a portion of this material from ethyl acetate-hexanes: mp 198°–200° C. $^1$H NMR (CDCl$_3$) δ2.30 (s, 6H), 3.60 (s, 6H), 4.80 (m, 3H), 5.20 (s, 1H), 6.71 (br s, 1H), 7.00–7.30 (m, 3H). Anal. Calcd. for C$_{18}$H$_{20}$ClNO$_5$: C, 59.10; H, 5.51; N, 3.83. Found: C, 58.78; H, 5.62; N, 3.94.

(f) Dimethyl 2,6-dimethyl-4-(2-tosyloxymethyl-5-chlorophenyl)-1,4-dihydropyridine-3,5-dicarboxylate (2f) and [4a(R,S), 9a(S,R)]Dimethyl 1-methylidine-3-methyl-6-chloro-2,4a-dihydro-9H-indeno[2,1-c]pyridine-4,9a-dicarboxylate To a 100 ml round bottom flask with stirring bar was added the compound (2e) (1.00 g, 2.73 mmol) and methylene chloride (40 ml). This solution was cooled to 0° C. and triethylamine (1.52 g, 15.00 mmol), 4-dimethylaminopyridine (10 mg, 0.08 mmol), and p-toluenesulfonylchloride (0.57 g, 3.00 mmol) were added. The mixture was stirred at 0° C. for 1 hour, then at room temperature for 15 hours. An additional 100 mg of p-toluenesulfonyl chloride was added and the mixture was stirred for 4 hours. The mixture was diluted with chloroform and washed with 5% aqueous HCl, saturated aqueous NaHCO$_3$, and brine. Drying (MgSO$_4$), filtration, and removal of the solvent in vacuo left compound (2f). This material was chromatographed on 100 g of silica gel using 2:3 ethyl acetate-hexanes as eluant to give pure compound (2f). $^1$H NMR (CDCl$_3$) δ2.25 (s, 6H), 2.40 (s, 3H), 3.49 (s, 6H), 4.83 (s, 1H), 5.49 (s, 2H), 5.95 (br s, 1H), 7.00–7.40 (m, 5H), 7.82 (d, 2H, J=9 Hz).

To a 100 ml round bottomed flask with stirring bar, reflux condenser and argon inlet was added compound (2f) (1.00 g, 1.92 mmol), dry DMF (30 ml), and finely powdered anhydrous potassium carbonate (3.50 g, 25.5 mmol). The reaction mixture was heated at 100° C. with vigorous stirring for 2 hours. The cooled reaction mixture was diluted with ethyl acetate (400 ml) and was washed with water (3×250 ml) and brine (250 ml). Drying (MgSO$_4$), filtration and removal of the solvent in vacuo gave a yellow oil. This material crystallized on standing. The oil crystals were recrystallized from ethyl acetate-hexanes, twice to give off white crystals of the desired product. The mother liquors were concentrated and chromatographed on 20 g of silica gel using 3:7 ethyl acetate-hexanes as the eluant. This provided additional product: 205°–208° C. $^1$H NMR (CDCl$_3$) δ2.33 (s, 3H), 3.20 (d, 1H, J=15 Hz) 3.60 (d, 1H, J=15 Hz), 3.65 (s, 3H), 3.70 (s, 3H), 4.37 (d, 1H, J=2 Hz), 47 (d, 1H, J=2 Hz), 4.62 (s, 1H), 6.10 (br s, 1H), 6.90 (s, 1H), 7.05 (br s, 2H). Anal. Calcd. for C$_{18}$H$_{18}$ClNO$_4$: C, 62.16; H, 5.22; N, 4.0. Found: C, 62.27; H, 5.56; N, 4.06.

EXAMPLE 3

Preparation of Dimethyl1-methylidene-3,9-dimethyl6-methoxy-2,4a-dihydro-9H-indeno[2,1-c]pyridine-4,9a-dicarboxylate and Dimethyl 1,3,9-trimethyl-6-methoxy-4a,9-dihydroindeno[2,1-c]pyridine-4,9a-dicarboxylate

(a) 1-Bromo-2-[2-(1,3-dioxalanyl)]-4-methoxybenzene (3a)

To a solution of 2-bromo-5-methoxybenzaldehyde (35.7 g, 166 mmol) and ethylene glycol (12.41 g, 200 mmol) in benzene (250 ml) was added p-toluenesulfonic acid monohydrate (200 mg) and the resulting solution was heated at reflux under a Dean-Stark trap for 20 hours. The benzene layer was separated from the aqueous layer and washed successively with saturated aqueous sodium bicarbonate, and brine, dried over anhydrous sodium sulfate and filtered. The filtrate was concentrated in vacuo to yield compound (3a), which was used directly in the next reaction.

(b) 2-[2-(1,3-dioxalanyl)]-4-methoxybenzaldehyde (3b)

To a solution of compound (3a) (38.87 g, 150 mmol) in dry tetrahydrofuran (500 ml) at −75° C. under nitrogen was added dropwise n-butyllithium (150 mmol) in hexane. The reaction mixture was stirred at −75° C. for an additional hour and a solution of N-formylpiperidine (180 mmol) in tetrahydrofuran (50 ml) was added dropwise. The reaction was allowed to warm to ambient temperature overnight. The reaction mixture was cooled to 0° C. and then quenched with saturated ammonium chloride (75 ml). The resulting mixture was then diluted with diethyl ether (750 ml) and the organic phase separated from the aqueous phase. The organic phase was washed with saturated ammonium chloride (4×100 ml) and brine (200 ml), dried over anhydrous sodium sulfate and filtered. The solvent was removed in vacuo and the resulting yellow oil purified by vacuum distillation to give compound (3b), bp 0.25 torr/13-4°–136°.

(c) 2-[2-(1,3-Dioxalanyl)]-4-methoxystyrene (3c)

To a solution of methyl triphenylphosphonium bromide (21.5 g, 266 mmol) in dry tetrahydrofuran (500 ml) at −70° C. under nitrogen was added dropwise n-butyllithium (252 mmol) in hexane. The temperature was allowed to rise to 0° C. gradually over 4 hours. Then compound (3b) (21.5 g, 103 mmol) in dry tetrahydrofuran (50 ml) was introduced dropwise at 0° C., and the reaction was allowed to warm to ambient temperature overnight. The solvent was removed in vacuo to yield a yellow residue which was purified by flash chromatography on silica gel eluted with hexane:ethyl acetate (9:1) to afford compound (3c) as a yellowish oil (R$_f$=0.35).

(d) 2-Ethenyl-5-methoxybenzaldehyde (3d)

To compound (3c) (14.9 g, 72.2 mmole) in dry acetone (500 ml) was added p-toluenesulfonic acid monohydrate (150 mg) and the resultant solution stirred at ambient temperature for 3 days. The solvent was removed in vacuo and the residue diluted with diethyl ether (500 ml), washed with dilute sodium bicarbonate, brine, dried over anhydrous sodium sulfate and filtered. The filtrate was concentrated in vacuo to yield an oil which was purified by flash chromatography on silica gel eluted with hexane:ethyl acetate (9:1) to yield compound (3d) as an oil ($R_f=0.4$).

(e) Dimethyl 2,6-dimethyl-4-(2-ethenyl-5-methoxyphenyl)-1,4-dihydropyridine-3,5-dicarboxylate (3e)

To compound (3d) (8.0 g, 49.3 mmol) in anhydrous methanol (50 ml) was added methyl 3-aminocrotonate (5.68 g, 49.3 mmol), methyl acetoacetate (5.72 g, 49.3 mmol), and concentrated ammonium hydroxide (1 ml) and the resulting solution heated at reflux under nitrogen for 4 days. The solvent was removed in vacuo and the residual material triturated with ether (20 ml) to give compound (3e) as a pale, yellowish solid, mp 141°–143°.

(f) Dimethyl 1-methylidene-3,9-dimethyl-6-methoxy-2,4a-dihydro-9H-indeno[2,1-c]pyridine-4,9a-dicarboxylate and Dimethyl 1,3,9-trimethyl-6-methoxy-4a,9-dihydroindeno[2,1-c]pyridine-4,9a-dicarboxylate To a solution of dimethyl 2,6-dimethyl-4-(2-ethenyl-5-methoxy)-1,4-dihydropyridine-3,5-dicarboxylate (2.0 g, 5.6 mmol) in chloroform (30 ml) at ambient temperature with stirring was added gaseous hydrogen chloride for 30 minutes. The reaction mixture was stirred at ambient temperature for about 16 hours, diluted with water (35 ml) and chloroform (100 ml) and then neutralized with concentrated ammonium hydroxide. The phases were separated and the aqueous phase extracted with chloroform. The combined organic phase was dried over sodium sulfate and concentrated in vacuo. The yellow residue was triturated with hexane:diethyl ether (1:2) to afford the desired product as a mixture of tautomers. mp 170°–172.5° C. Analytically pure product was obtained by recrystallization from cyclohexane, mp 170°–172.5° C. Anal. Calc'd for $C_{20}H_{23}NO_5$ C, 67.21; H, 6.49; N, 3.92. Found C, 67.50; H, 6.65; N, 3.99.

EXAMPLES 4–20 (Hypothetical)

Utilizing the general procedure of Examples 1, 2 or 3 and starting with appropriately substituted dihydropyridine the following compounds of the formula (I) are prepared.

| Compound | R | $R^1$ | $R^2$ | $R^3$ | $R^4$ | $R^5$ | X | Y |
|---|---|---|---|---|---|---|---|---|
| 4 | H | Me | Et | Et | Me | Me | H | H |
| 5 | H | Et | Et | Et | Et | H | H | H |
| 6 | Me | H | Me | Me | Et | Et | H | OMe |
| 7 | CH$_2$Ph | Me | Me | Me | Me | Me | H | H |
| 8 | Me | Me | Et | Et | Me | H | H | NO$_2$ |
| 9 | H | Me | Me | Me | Me | Et | H | CF$_3$ |
| 10 | Et | Me | phenyl | phenyl | Me | H | H | H |
| 11 | Et | Me | Me | Me | Me | Me | OMe | H |
| 12 | H | —CH$_2$CH=CH$_2$ | Me | Me | Me | H | Cl | Cl |
| 13 | H | —CH$_2$OH | Et | Et | Me | H | H | H |
| 14 | H | cyclohexyl | Me | Me | Me | H | OMe | H |
| 15 | H | Me | —CH$_2$CH=CH$_2$ | —CH$_2$CH=CH$_2$ | Me | H | H | Me |
| 16 | H | Me | —CH$_2$CH$_2$OH | Me | Me | Me | H | Cl |
| 17 | H | Me | Me | —CH$_2$CH$_2$OCH$_2$CH$_2$OCH$_3$ | Me | H | H | H |
| 18 | H | Me | —CH$_2$CH$_2$NMe$_2$ | —CH$_2$CH$_2$NMe$_2$ | Me | H | H | CF$_3$ |
| 19 | H | Me | CH$_2$N(CH$_3$)CH$_2$Ph | Et | Me | H | H | H |
| 20 | H | Me | CH$_2$N-piperidinyl | CH$_2$N-piperidinyl | Me | H | H | H |

It should be noted that for the preparation of Compounds 13 and 16 the hydroxyalkyl moiety is acylated with acetic anhydride prior to cyclization and then deacylated with sodium hydroxide.

EXAMPLE 21

As a specific embodiment of a composition of this invention an active ingredient, such as [4a(R,S),9a(S,R)-]dimethyl 1-methylidine-3-methyl-2,4a-dihydro-9H-indeno[2,1-c]pyridine-4,9a-dicarboxylate is formulated to yield 5000 compressed tablets, each containing 50 mg of the active ingredient, as follows:
Active ingredient: 250 grams
Starch: 70 grams Dibasic calcium phosphate hydrous: 500 grams
Calcium stearate: 2.5 grams

What is claimed is:

1. A compound represented by the following general structural formula (I):

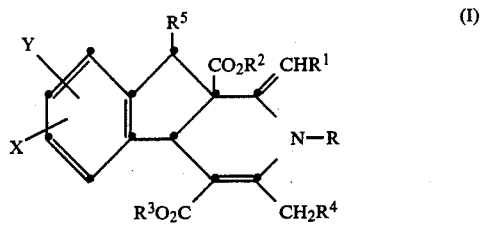

wherein:
R is hydrogen, $C_1$–$C_8$ alkyl or benzyl;
$R^1$ and $R^4$ independently are hydrogen, $C_1$–$C_8$ alkyl, $C_2C_8$ alkenyl, $C_1$–$C_8$ cycloalkyl, $C_1$–$C_8$ hydroxyalkyl;
$R^2$ and $R^3$ independently are $C_1$–$C_8$ alkyl, $C_2$–$C_8$ alkenyl, $C_3$–$C_8$ cycloalkyl, $C_1$–$C_8$ hydroxyalkyl, $C_1$–$C_8$ dihydroxyalkyl, $C_2$–$C_8$ alkoxyalkyl, $C_3$–$C_8$ alkoxy(alkoxyalkyl), $C_1$–$C_8$ aminoalkyl wherein the amino group is $NR^6R^7$ in which $R^6$ and $R^7$ independently are hydrogen, $C_1$–$C_8$ alkyl, $C_7$–$C_{14}$ phenylalkyl or $R^6$ and $R^7$ together with the N atom is piperidyl;
$R^5$ is hydrogen or $C_1$–$C_8$ alkyl; and
X and Y independently are hydrogen, $C_1$–$C_8$ alklyl, $C_1$–$C_8$ alkoxy, $CF_3$, cyano, nitro or halo, of a pharmaceutically acceptable salt thereof.

2. A compound of claim 1 wherein:
R is hydrogen or $C_1$–$C_8$ alkyl;
$R^1$ and $R^4$ independently are hydrogen or $C_1$–$C_8$ alkyl;
$R^2$ and $R^3$ independently are $C_1$–$C_8$ alkyl or $C_1$–$C_8$ amino alkyl wherein the amino group is $NR^6R^7$ in which $R^6$ and $R^7$ independently are hydrogen, $C_1$–$C_8$ alkyl or $C_7$–$C_{14}$ phenylalkyl;
$R^5$ is hydrogen or $C_1$–$C_8$alkyl; and X and Y independently are hydrogen, $C_1$–$C_8$ alkoxy, $CF_3$, cyano, nitro or halo.

3. A compound of claim 2 wherein: $R^1$, $R^2$, $R^3$ and $R^4$ are independently hydrogen or $C_1$–$C_8$ alkyl; and X and Y are hydrogen, or nitro, and $R^5$ is hydrogen or methyl.

4. A compound of claim 3 which is dimethyl 1-methylidene-3-methyl-2,4a-dihydro-9H-indeno[2,1-c]pyridine-4,9a-dicarboxylate.

5. A compound of claim 3 which is dimethyl1-methylidene-3-methyl-6-chloro-2,4a-dihydro-9H-indeno[2,1-c]pyridine-4,9a-dicarboxylate.

6. A compound of claim 3 which is dimethyl-6-methoxy-2,4a-dihydro-9H-indeno[2,1-c]pyridine-4,9a-dicarboxylate.

7. A pharmaceutical composition, useful in the treatment of cardiovascular disorders caused by high cellular concentration of calcium comprising a nontoxic amount of a compound according to claim 1 in an admixture with a pharmaceutically acceptable carrier wherein said amount is such that will therapeutically effectively reduce the cellular concentration of calcium.

8. A method of treatment for cardiovascular disorders caused by high cellular concentration of calcium which comprises administering to a subject in need of such treatment a nontoxic therapeutically effective amount of a compound according to claim 1, said amount being such that will therapeutically effectively reduce the cellular concentration of calcium.

9. A process for the preparation of the compounds of claim 1 which comprises treating a compound of the following formula:

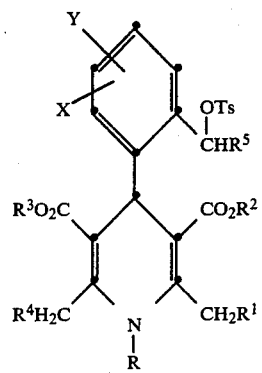

wherein R, $R^1$, $R^2$, $R^3$, $R^4$, $R^5$, X and Y are defined in claim 1, and Ts is a tosyl radical, with a base under anhydrous conditions.

10. A process for the preparation of the compounds of claim 1 wherein X or Y is $C_1$–$C_8$ alkoxy which comprises treating a compound of the following formula:

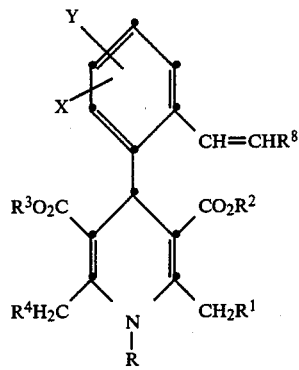

wherein R, $R^1$, $R^2$, $R^3$, $R^4$ and Y are defined in claim 1 and is hydrogen or $C_1$–$C_7$ alkyl with protic acid in an inert solvent.

* * * * *

UNITED STATES PATENT AND TRADEMARK OFFICE
CERTIFICATE OF CORRECTION

PATENT NO. : 4,593,033

DATED : June 3, 1986

INVENTOR(S) : GEORGE D. HARTMAN, ET AL.

It is certified that error appears in the above—identified patent and that said Letters Patent is hereby corrected as shown below:

Column 13, Claim 1, line 20, "$C_2C_8$" should be

-- $C_2$-$C_8$ --

Column 13, Claim 1, line 28, "$C_1$--$C_8$" should be

-- $C_1$-$C_8$ --

Column 13, Claim 2, line 32, "of" should be -- or --

Column 13, Claim 3, after hydrogen, insert -- $C_1$-$C_8$ alkoxy --

Column 14, Claim 10, line 56, after "and" insert

-- $R^8$ --

Signed and Sealed this

Twenty-eighth Day of October, 1986

[SEAL]

*Attest:*

DONALD J. QUIGG

*Attesting Officer*   *Commissioner of Patents and Trademarks*